(12) United States Patent
Edmonson et al.

(10) Patent No.: US 7,771,987 B2
(45) Date of Patent: Aug. 10, 2010

(54) ACOUSTIC WAVE SENSOR ASSEMBLY UTILIZING A MULTI-ELEMENT STRUCTURE

(76) Inventors: Peter J. Edmonson, 138 Stone Church Road East, Hamilton, Ontario (CA) L9B 1A9; William D. Hunt, 109 Kirk Crossing Dr., Decatur, GA (US) 30030; Christopher D. Corso, 493 N. Highland Ave., Apt. #31, Atlanta, GA (US) 30307; Anthony Dickherber, 356 Foxfire Dr., Smyrna, GA (US) 30082; Marie E. Csete, 1892 Mason Mill Rd., Decatur, GA (US) 30033

( * ) Notice: Subject to any disclaimer, the term of this patent is extended or adjusted under 35 U.S.C. 154(b) by 285 days.

(21) Appl. No.: 11/822,045

(22) Filed: Jul. 2, 2007

(65) Prior Publication Data

US 2009/0009268 A1 Jan. 8, 2009

(51) Int. Cl.
*G01N 33/552* (2006.01)
(52) U.S. Cl. ............... 435/287.2; 73/24.06; 310/313 R; 310/313 B; 310/340; 436/524; 436/527
(58) Field of Classification Search ........................ None
See application file for complete search history.

(56) References Cited

U.S. PATENT DOCUMENTS 5,448,125 A * 9/1995 Chu ..................... 310/313 A
5,814,525 A * 9/1998 Renschler et al. ........... 436/524
6,848,295 B2 * 2/2005 Auner et al. ............... 73/24.06

* cited by examiner

*Primary Examiner*—Christopher L Chin
(74) *Attorney, Agent, or Firm*—Steven M. Greenberg, Esq.; Carey Rodriguez Greenberg & Paul LLP

(57) ABSTRACT

An acoustic wave sensor assembly includes piezoelectric material, a first acoustic wave resonator element structure mounted on the piezoelectric material for interacting with an electrical signal, the acoustic wave resonator element structure being operable to interact with an acoustic wave propagating within the piezoelectric material to produce a first frequency response. Further acoustic wave resonator element structures are mounted on the piezoelectric material for interacting with electrical signals, the further acoustic wave resonator element structures being operable to interact with further acoustic waves propagating within the piezoelectric material to produce subsequent frequency responses. The first acoustic wave resonator element structure and further acoustic wave resonator element structures are combined to form a ladder or lattice filter network to produce an overall frequency response. Sensitive areas are mounted on the piezoelectric material and associated with the acoustic wave resonator element structures which, if predetermined effects to be sensed or detected are present, are modified thereby to control the nature of the frequency responses with resultant specific perturbations of the combined frequency response and thereby provide information with respect to the predetermined effects to be sensed or detected.

18 Claims, 10 Drawing Sheets

(a)

(b)

(a)

(b)

Paired Multi-Element
Configuration
600

ACOUSTIC WAVE SENSOR ASSEMBLY UTILIZING A MULTI-ELEMENT STRUCTURE

FIELD OF INVENTION

This invention relates to acoustic wave sensor assemblies.

BACKGROUND OF THE INVENTION

Acoustic wave sensors for measuring the properties of physical, chemical and biological effects are well known. Such sensors can be categorized as oscillator based or RFID based. Both systems take advantage of the physical, chemical and biological effects perturbing acoustic wave velocity within piezoelectric material. With oscillator based acoustic wave sensors, a delta frequency (Δf) offset is obtained according to the Sauerbrey equation. RFID based acoustic wave sensors can also detect a delta frequency (Δf) as well as due to velocity change, change in time (Δt), change in frequency (Δf), change in phase (Δφ) or a change in the correlation pattern (Δc).

Difficulties with oscillator based and RFID based systems become evident when multiple measurements of physical, chemical and biological effects are desired, forcing the system to become complex. For oscillator based systems, either multiple oscillators must be used or a complex switching network provided to switch in the various acoustic wave devices as the feedback elements of a single oscillator. Attention must also be given to the transient and settling times of a single oscillator. RFID based systems have upper limits related to how many arrays can be placed on a single acoustic wave RFID device.

Oscillator based sensor detection systems utilizing acoustic wave devices as part of the feedback element present concerns with respect to their operating characteristics, especially if more than one acoustic wave device is used. A first concern involves the stability of the oscillator due to thermal drift and load pulling of the amplifier portions of the circuit. Another concern is instability due to possible coupling of modes between adjacent acoustic wave devices which may introduce injection-locking phenomena from stray coupling within the oscillators. For a typical acoustic wave sensor system, at least two or more oscillator circuits are used, one for a reference acoustic wave and the others for measuring specified effects. This can null out any temperature, physical shock, pressure or other attributes that the acoustic wave devices are subjected to. Concern with injection locking within an array of detection oscillators requires both skilled electronic and mechanical design in order to shield or separate possible influencing signals.

The following publications outline the sensitivity of oscillators subjected to external injected signals:

P. J. Edmonson et al., "Injection locking techniques for a 1 GHz digital receiver using acoustic wave devices," IEEE Transactions on Ultrasonics, Ferroelectrics and Frequency Control, vol. 39, no. 5, pp. 631-637, September 1992.

P. J. Edmonson et al, "The application of injection-locked oscillators to wireless communication systems," Proceedings of the 1992 Canadian Conference on Electrical and Computer Engineering, Toronto, ON, pp. MM2.2.1-MM2.2.4, 13-16 Sep. 1992.

Possibly the largest concern with an oscillator detection system is the loss of possible information with respect to detected substances due to an averaging effect of the oscillator. Hunt et al., "Time-dependent signatures of acoustic wave biosensors," Proceedings of the IEEE, vol. 91, pp. 890-901, 2003, developed an analytical relationship from the complex reciprocity relation and time-dependent perturbation theory from the modified Sauerbrey equation.

$$\Delta f = -\frac{2 f_u^2 h_f}{\sqrt{\rho_q \mu_q}} \left[ \Delta \rho - \frac{\Delta \mu}{V_s^2} \right]$$

Where $V_s$ is the acoustic velocity; $\rho$ is the density of the film; $h_f$ is the thickness of the film; $\mu_q$ and $\rho_q$ are the shear stiffness and density of the quartz crystal, respectively; $\mu$ is the stiffness of the film; $\Delta$ is the difference between perturbed and unperturbed (denoted by subscript u) quantities. The stiffness of the film, $\mu$, is affected by the conformational change of the recognition molecules. Conformational change is the change in the molecular structure of the MRE. In electrical terms it is equivalent to the phase change of the MRE. If the detected substances vary slightly this would also cause a slight change in the molecular structure of the receptor molecule and several values of $\Delta \mu$ would exist, such as $\Delta \mu_a$, $\Delta \mu_b$, $\Delta \mu_c$, etc. Edmonson et al., "SAW-based carrier recovery without phase ambiguity for 915 MHz BPSK wireless digital communications," 1992 IEEE Ultrasonics Symposium Proceedings, Tucson, Ariz., pp. 241-244, 20-23 Oct. 1992 has demonstrated that, within an oscillator circuit, independent changes are averaged to produce a single frequency output.

Other concerns that this invention addresses are the problems associated with the independent nature of the several amplifier components used within multiple oscillator circuits. These amplifier components are subjected to internal thermal cycling which changes their operating characteristics and affects the frequency stability of the oscillators. To reduce overall complexity, only one amplifier component is used within one oscillator and the various acoustic wave devices are multiplexed to this amplifier component. This then introduces load pulling, since each acoustic wave device is not identically impedance matched with respect to the other acoustic wave devices, and frequency instability is introduced.

The present invention utilizes a passive multi-element structure as the basis for its detection system. Further, the invention utilizes a swept frequency response which broadens the investigative range and can detect anomalies of the physical, chemical and biological effects which would be challenging to accomplish within an oscillator based detection system but can be implemented within an interrogation type sensor system such as an RFID sensor application.

SUMMARY OF INVENTION

According to the present invention, ladder and lattice type structures can each have independent segments of an array positioned on the multiple elements of each of the ladder and lattice structures and by interrogating such structures the identification and characterization of certain physical, chemical and biological effects can be made. Such a structure minimizes the use of active components and can sense physical, chemical and biological effects over a broader frequency range. One of the many possible uses of the present invention is the real time detection of complex diseases, such as sepsis where several different recognition elements are required for identification.

Accordingly, the present invention provides an acoustic wave sensor assembly including:

piezoelectric material;

a first acoustic wave resonator element structure mounted on the piezoelectric material for interacting with an electrical signal;

said acoustic wave resonator element structure being operable to interact with an acoustic wave propagating within the piezoelectric material to produce a first frequency response;

further acoustic wave resonator element structures mounted on the piezoelectric material for interacting with electrical signals;

said further acoustic wave resonator element structures being operable to interact with further acoustic waves propagating within the piezoelectric material to produce subsequent frequency responses;

said first acoustic wave resonator element structure and further acoustic wave resonator element structures being combined to form a ladder or lattice filter network to produce an overall frequency response; and sensitive areas mounted on the piezoelectric material and associated with the acoustic wave resonator element structures which, if predetermined effects to be sensed or detected are present, are modified thereby to control the nature of the frequency responses with resultant specific perturbations of the combined frequency response and thereby provide information with respect to the predetermined effects to be sensed or detected.

This invention is ideal for uses where multiple physical, chemical and biological effects need to be measured to identify or characterize a specific event. Ladder and lattice structures may be composed of several series and shunt resonator devices. Ladder filters are well known in the communications field and are used in cell phones, pagers, wireless modems and other transceiver applications. Each series or shunt element of the ladder or lattice sensor structure can be configured to independently measure a physical, chemical or biological effect such that the complete ladder or lattice structure can collectively measure the multiple physical, chemical and biological effects which are required to identify or characterize a specific event.

One use of this invention is to utilize two or more orthogonal or semi-orthogonal molecular recognition elements (MREs) as described by Edmonson et al, "DIFFERENTIATION AND IDENTIFICATION OF ANALOGOUS CHEMICAL OR BIOLOGICAL SUBSTANCES WITH BIOSENSORS" US Patent Application US2006/0213271 A1, on the ladder or lattice structures. A typical scenario would place MRE #1 on the series elements and the orthogonal or semi-orthogonal MRE #2 on the shunt elements of a ladder structure. The repetition of the MRE #1 and MRE #2 material would improve the detection statistics of the sensor.

Another use is the detection and identification of various diseases by using an acoustic wave sensor with a multi-element structure in accordance with the present invention to detect and identify several biological or equivalent biomarkers associated with the indicators and precursors associated with these diseases. An example of a single biomarker detector is outlined by C. D. Corso and W. D. Hunt et al, "Real-time detection of mesothelin in pancreatic cancer cell line supernatant using an acoustic wave immunosensor," Cancer Detection and Prevention Journal, vol. 30, pp. 180-187, 2006. A system to measure several indicators and precursors at once in real time would be useful in the detection of sepsis, which is a cascading failure of organ systems, usually initiated by infection of the blood, then exacerbated by a massive, injurious inflammatory response.

This invention improves on previous efforts of utilizing multiple arrays of sensors by introducing a new type of arrangement that incorporates an array within its own structure. This structure is passive to eliminate any instability found in active circuits, eliminates any averaging effects found in oscillator sensor circuits, introduces a means to include sensed information obtained over a swept frequency range and can be readily adapted for wireless RFID sensor applications. The composition of this structure includes cascading certain resonant structures which includes micro-electrical-mechanical-systems (MEMS) such as thin film bulk acoustic resonators (FBARs), surface acoustic wave (SAW) resonators and other acoustic wave resonators such as bulk acoustic wave (BAW), leaky surface acoustic wave (LSAW) and other known acoustic modes of propagation described in publications such as, C. K. Campbell, Surface Acoustic Wave Devices for Mobile and Wireless Communications, Academic Press, 1998.

DESCRIPTION OF THE DRAWINGS

Embodiments of the invention will now be described, by way of example, with reference to the accompanying drawings, of which.

DESCRIPTION OF PREFERRED EMBODIMENTS

Figure 1:
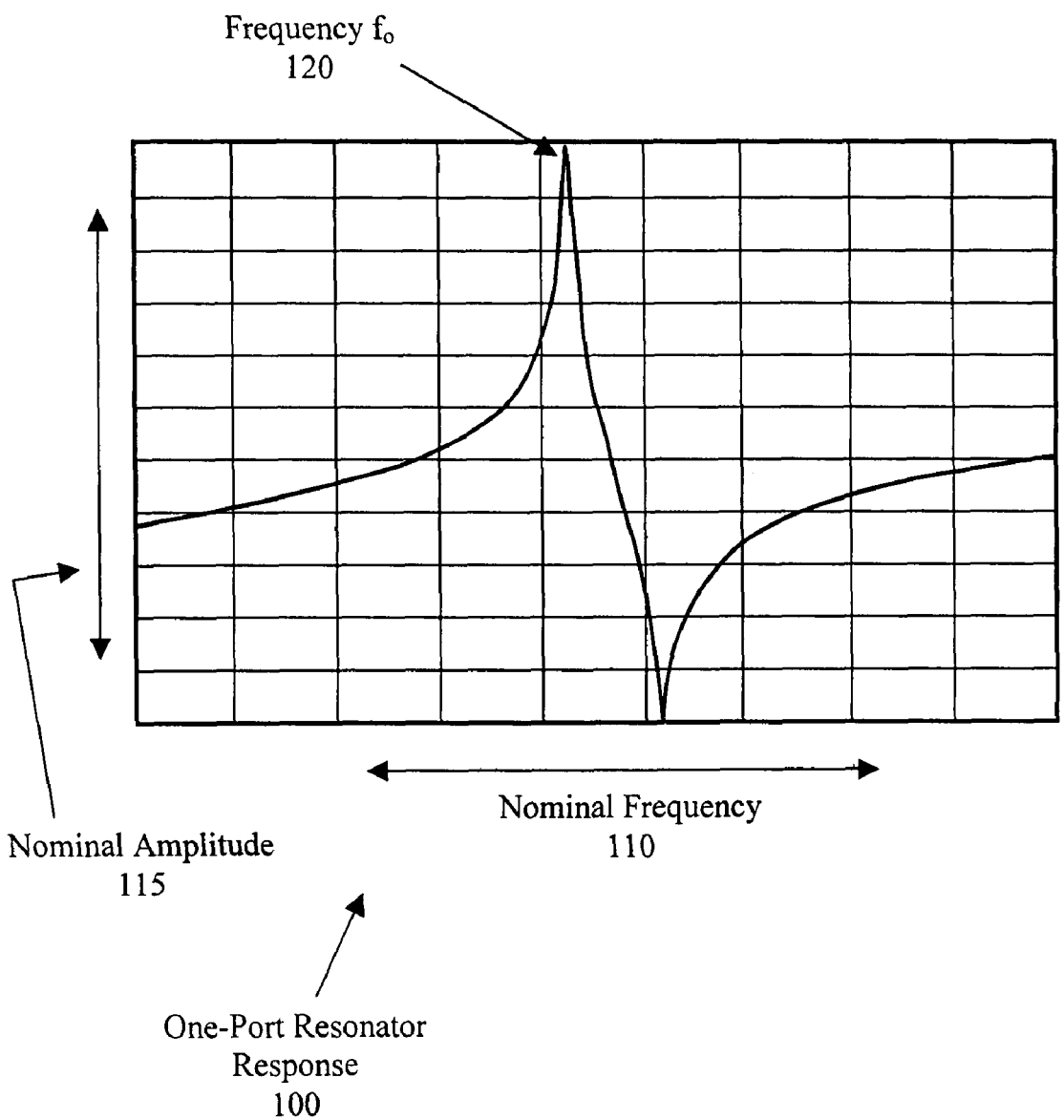
FIG. 1 is a graph showing a one-port resonator response.

Referring to the drawings, resonators are typically high Q devices in that they achieve an amplitude peak and valley within a narrow frequency range in the impedance spectrum. A typical one-port resonator response 100 is shown in FIG. 1, with the x-axis representing the nominal frequency 110 and the y-axis representing the nominal amplitude 115. The one-port resonator response 100 is fixed at frequency $f_o$ 120.

Figure 2:
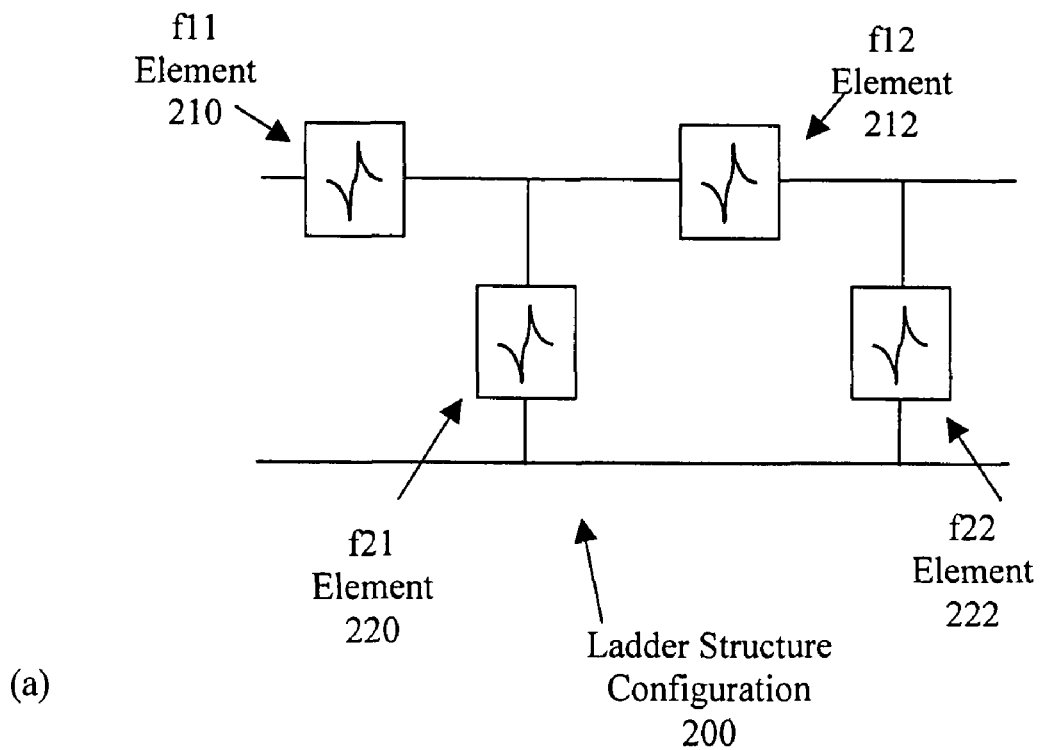
FIG. 2(a) is a schematic view of a ladder structure configuration.
FIG. 2(b) is a similar view of a lattice structure configuration.
Figure 2:
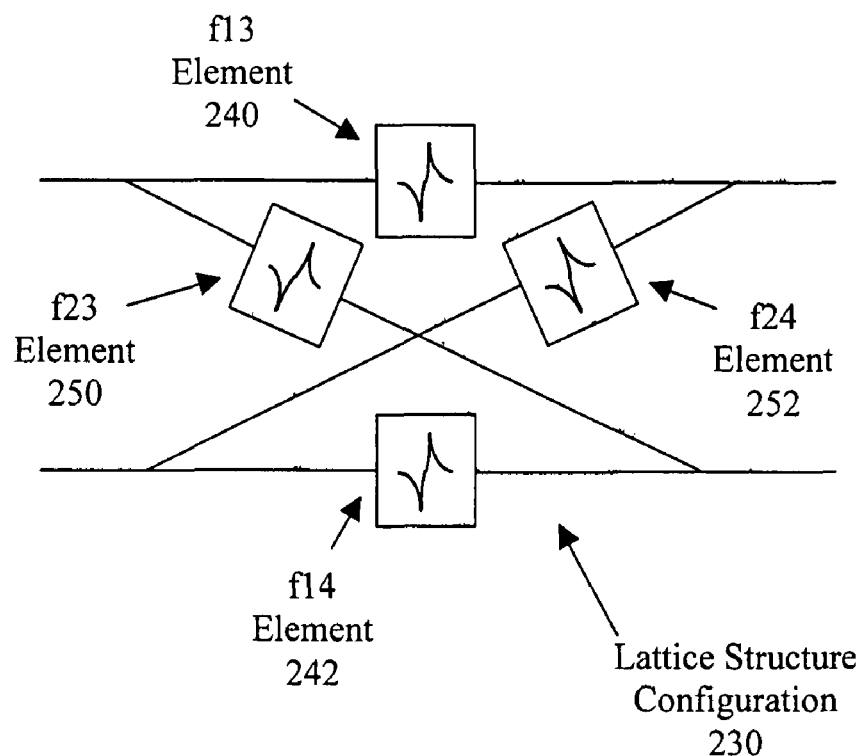

Communication systems including digital radios have utilized ladder and lattice type structures as filters for a number of years. Numerous publications, such as Lakin et al, Thin Film Resonator Technology, IEEE 2003 FCS-EFTF, Paper We1A-4 (Invited) May 5-8, 2003, describe how such ladder and lattice structures benefit the communications industry. A similar approach is made with this invention to benefit the sensor industry. FIG. 2(a) shows a ladder structure configuration 200 which comprises several resonator elements. Each of the series resonator elements, namely f11 element 210 and f12 element 212, are individual resonators configured such that each of their resonant peaks are at a frequency $f_o$ 120, as shown in FIG. 1. Similarly, each of the shunt resonator elements namely as f21 element 220 and f22 element 222, are individual resonators configured such that each of their resonant peaks are at a frequency $f_1$ which is slightly offset from frequency $f_o$ 120. Thus, in the ladder structure configuration 200, a total of four resonator elements are utilized. It should be noted however that a fundamental ladder configuration can be constructed with a single series element and a single shunt element, and further derivations of ladder configurations can be constructed with several series elements and several shunt elements suitably configured.

FIG. 2(b) shows a related lattice structure configuration 230. Each of the series resonator elements, namely f13 element 240 and f14 element 242, are individual resonators configured such that each of their resonant peaks are at a frequency $f_o$ 120, as shown in FIG. 1. Similarly, each of the cross-shunt resonator elements, namely f23 element 250 and f24 element 252, are individual resonators fashioned such that each of their resonant peaks are at a frequency $f_1$, which is slightly offset from frequency $f_o$ 120. Thus, in the lattice structure configuration 230, a total of four resonator elements are utilized. It should be noted that further derivations of lattice configurations can be constructed with several series elements and several cross-shunt elements suitably configured.

A common design requirement for filter applications in the communications industry is to achieve a smooth pass band such that a signal of one particular frequency within the desired frequency band will be regarded with the same attenuation as other signals at different frequencies within the same pass band. In typical communications ladder filter design, the zero of the series resonator must be directly aligned with the pole of the shunt resonator along with other matching techniques to ensure a flat pass band. The tolerance for the resonant frequencies of the components is typically very stringent, therefore reducing overall manufacturing yield. However, for sensor applications, not only is a smooth pass band not required, it is actually less desirable because the ripples in the pass band will aid in the detection process. When the frequency response of a ladder or lattice sensor structure is shifted slightly either up or down in frequency due to perturbation effects, the combination of the shifted response along with a non-shifted reference response from a similar reference ladder or lattice structure results in an overall different signal response characteristic of the frequency shift and can be used in identifying sensor detection events. Also, within a sensor configuration, tolerances can be less stringent since a difference between a reference and measured responses is required. This will lower the cost of such sensing devices, since the manufacturing yield will be higher.

Figure 3:
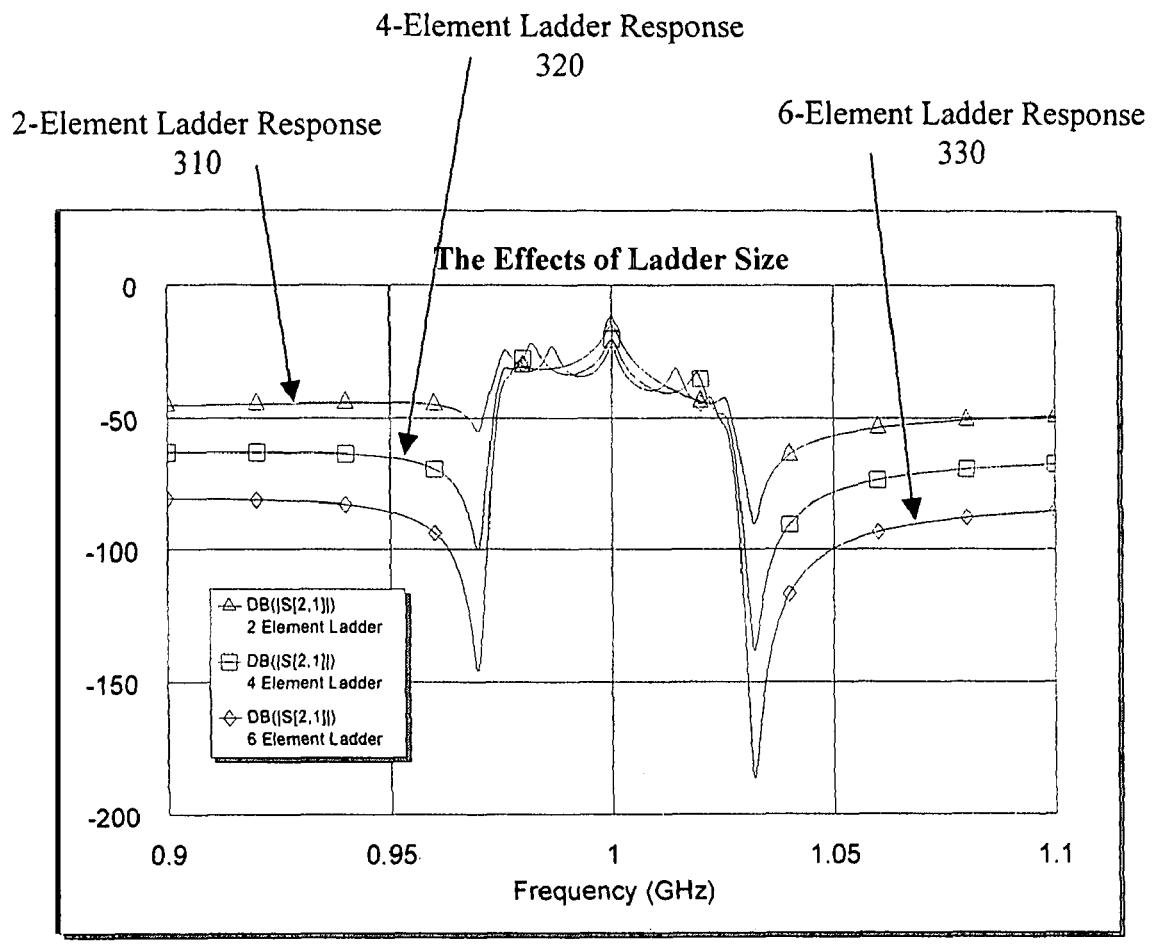
FIG. 3 is a graph showing frequency responses of multi-element ladder structures.

The general shape of the frequency responses of multi-element ladder structures 300 is illustrated in FIG. 3, with the center frequency of approximately 1 GHz chosen for illustrative purposes. A comparison is made between the responses of a two-element ladder response 310 similar to that the ladder structure configuration 200 shown in FIG. 2(a), a 4-element ladder response 320 and a 6-element ladder response 330. The pass band ripple, the depth of the nulls and the attenuation of the out of band response are a function of the number of ladder elements selected for the configuration.

How the ladder or latter structure responds to a perturbation of an elemental resonator depends on where the elemental resonator is placed within the ladder or lattice structure. Unlike ladder, lattice or other filter structures such as acoustic wave filters used in communication applications, such multi-element structures are not symmetrical in operation when used for sensor applications. Resonator structures positioned nearer to the input stimulus have more impact, when perturbed, on the outcome of the sensor frequency response than resonator structures positioned further away from the input stimulus. This leads to a selection of where in the multi-element structure certain perturbations should take place, for example placing the most sensitive perturbation closest to the input stimulus to maximize its affect.

Figure 4:
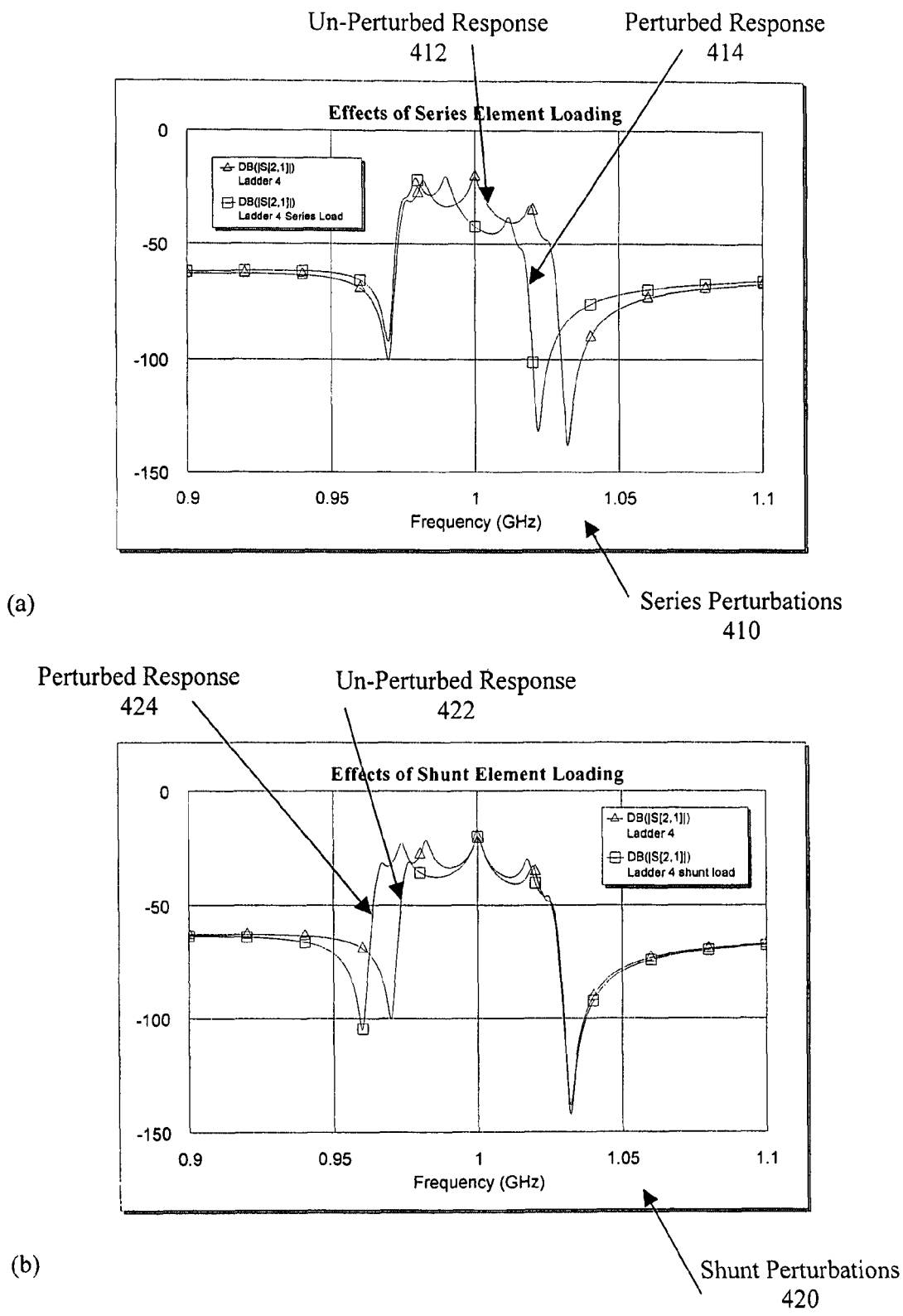
FIG. 4(a) is a graph showing a multi-element ladder frequency response with perturbation of series elements.
FIG. 4(b) is a multi-element ladder frequency response with perturbation of shunt elements.

The perturbations can occur on the series element resonators 210, 212, the shunt element resonators 220, 222, or a combination thereof. The effect on the multi-element ladder frequency response 400 with (a) series perturbations 410 and (b) shunt perturbations 420 is shown in FIGS. 4(a) and 4(b). The series perturbations 410 illustrate a comparison between an unperturbed response 412 and a perturbed response 414 of the series elements of a 4-element ladder structure similar to that shown in FIG. 2 (a). The low frequency side, up to the beginning of the pass bands of the unperturbed response 412 and the perturbed response 414 remain relatively unchanged. The high frequency side beyond the beginning of the pass bands begins to show a difference between the unperturbed response (412) and the perturbed response (414), indicating that a measurement of this difference would correlate to the amount of perturbation which took place on the series elements of the perturbed 4-element ladder structure.

Similarly, the shunt perturbations 420 illustrate a comparison between an unperturbed response 422 of the shunt elements of a 4-element ladder structure similar to that shown in FIG. 2(a). The high frequency side, beyond the pass bands of the unperturbed response 422 and the perturbed response 424, remain relatively unchanged. However, the response below the upper pass band edge begins to show a difference between the unperturbed response 422 and the perturbed response 424, indicating that a measurement of this difference would correlate to the amount of perturbation which took place on the shunt elements of the perturbed 4-element ladder structure. Similar perturbed and unperturbed effects of an n-element ladder structure would likewise occur.

Figure 5:
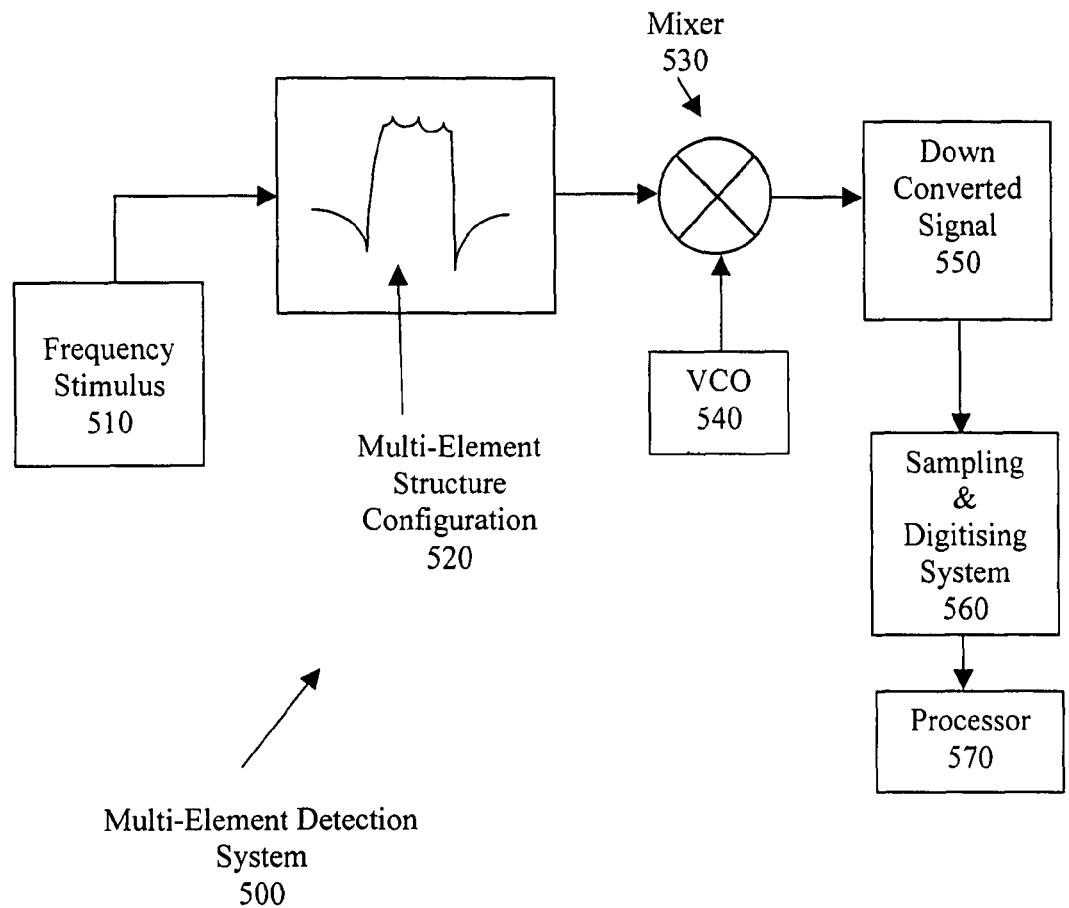
FIG. 5 is a schematic view of a multi-element detection system.

One example of an acoustic wave sensor utilizing a multi-element detection system 500 is shown in FIG. 5. A frequency stimulus 510 excites a multi-element structure configuration 520. The preferred frequency stimulus 510 is a swept frequency in which the start frequency and stop frequency of the frequency stimulus (510) include the nominal frequency range of the individual elemental resonators and the potential perturbed frequency responses of the multi-element structure. One method of providing the frequency stimulus 510 is to construct a SAW frequency modulated (FM) chirp generator as described in, Edmonson et al., "Mode selection in a multimode SAW oscillator using FM chirp mixing signal injection," IEEE Trans. On Ultrasonics, Ferroelectrics and Frequency Control, Vol. UFFC-35, no. 3, pp. 390-395, May 1988.

The output of the multi-element structure configuration 520 functions as the input to a mixer 530, which also uses a signal input from a voltage controlled oscillator (VCO) 540 to produce a modified down converted signal 550 at a lower frequency range than the resonant frequencies of the multi-element structure configuration 520. This down converted signal 550 is then suitably conditioned, sampled and digitised within a sampling and digitising system 560. The binary equivalent of the down converted signal 550 then acts as the input to a digital processor 570. The processor 570 can then utilize a suitable algorithm to detect the magnitude and phase features of the frequency response characteristics of the multi-element structure configuration 520 or any changes to the response.

Figure 6:
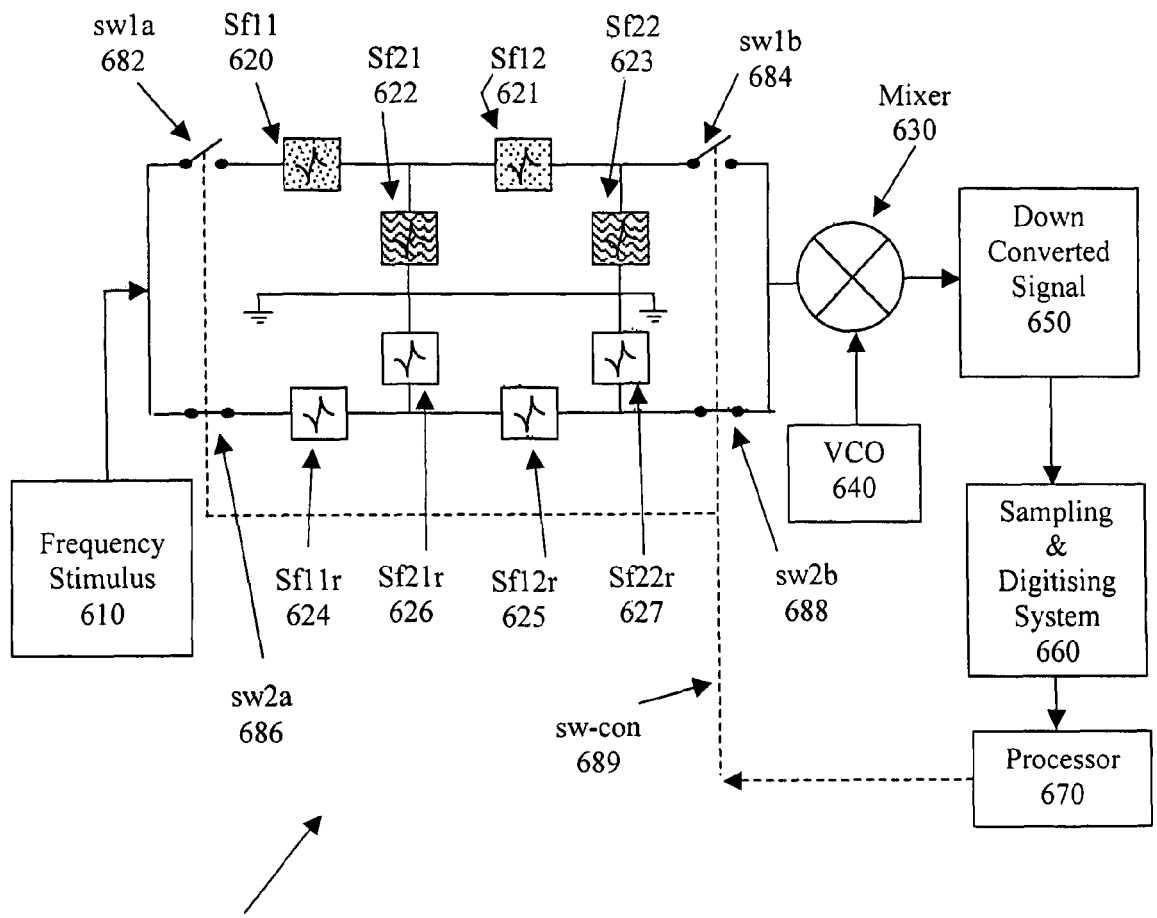
FIG. 6 is a similar view of a paired multi-element configuration.

The multi-element detection system 500 can be modified to produce a paired multi-element configuration 600 shown in FIG. 6. Instead of a single multi-element configuration, paired sets of two separate multi-element structure configurations are used. Typically, one multi-element structure configuration comprises series resonators Sf11 620 and Sf12 621 and shunt resonators Sf21 622 and Sf22 623 and has the purpose of sensing the physical, chemical and biological effects. The other multi-element structure comprises series resonators Sf11r 624 and Sf12r 625 and shunt resonators Sf21r 626 and Sf22r 627 and has the purpose of providing a reference signal. Even though this paired multi-element configuration depicts a total of two series and two shunt elements per structure, the same kind of arrangement can be used for an n-element structure. Also, the individual resonator elements may be located on the same body of substrate material or may be located independently on their own separate body of substrate material or a combination thereof.

According to one embodiment of the invention, suitable sensitive areas, such as molecular recognition element (MRE) material, can be placed on each of the multiple series elements Sf11 620 and Sf12 621, and may be placed on each of the multiple shunt elements Sf21 622 and Sf22 623. These sensitive areas associated with the multiple series elements Sf11 620 and Sf12 621 need not be identical in nature and may be different. This is because of the configuration of a ladder or lattice structure in which the frequency response changes differently if each of the multiple series elements Sf11 620 and Sf12 621 were to independently change. The processor 570 of FIG. 5 may utilize a suitable algorithm to detect the independent changes of the frequency response and determine which of the sensitive areas, including both, were perturbed. This same analogy can also be applied to the multiple shunt elements Sf21 622 and Sf22 623 and to ladder and lattice structures comprising n-elements.

A matrix of switches sw1a 682, sw1b 684, sw2a 686 and sw2b 688 are controlled by the processor 670 via a switch controller bus (sw-con) 689, to divert the frequency stimulus 610 to each of the paired multi-element structures and to direct the outputs from the paired multi-element structures to the input of the mixer 630. The mixer 630 uses another suitable frequency input from a VCO 640, to produce a modified down converted signal 650 at a lower frequency range than the resonant frequencies of the paired multi-element structures. This selected down converted signal 650 is then suitably conditioned, sampled and digitised within a sampling and digitising system 660. The binary equivalent of the selected down converted signal 650 then acts as the input to a digital processor 670. The processor 670 can then detect the frequency response characteristics of each of the paired multi-element structures and produce data indicating a change due to the interaction of the sensitive areas within the detecting multi-element structures. It may not appear initially to be clear why a reference multi-element structure configuration is required in that it would appear that the processor would measure and store the data at the initialisation of the detecting sequence and then use this digital stored data as the reference to any further change. The advantage of utilizing a paired multi-element configuration 600 with one of the pairs acting as a reference is that this can null out any global attributes that all of the acoustic wave resonators are subjected to within the detection sequence.

Figure 7:
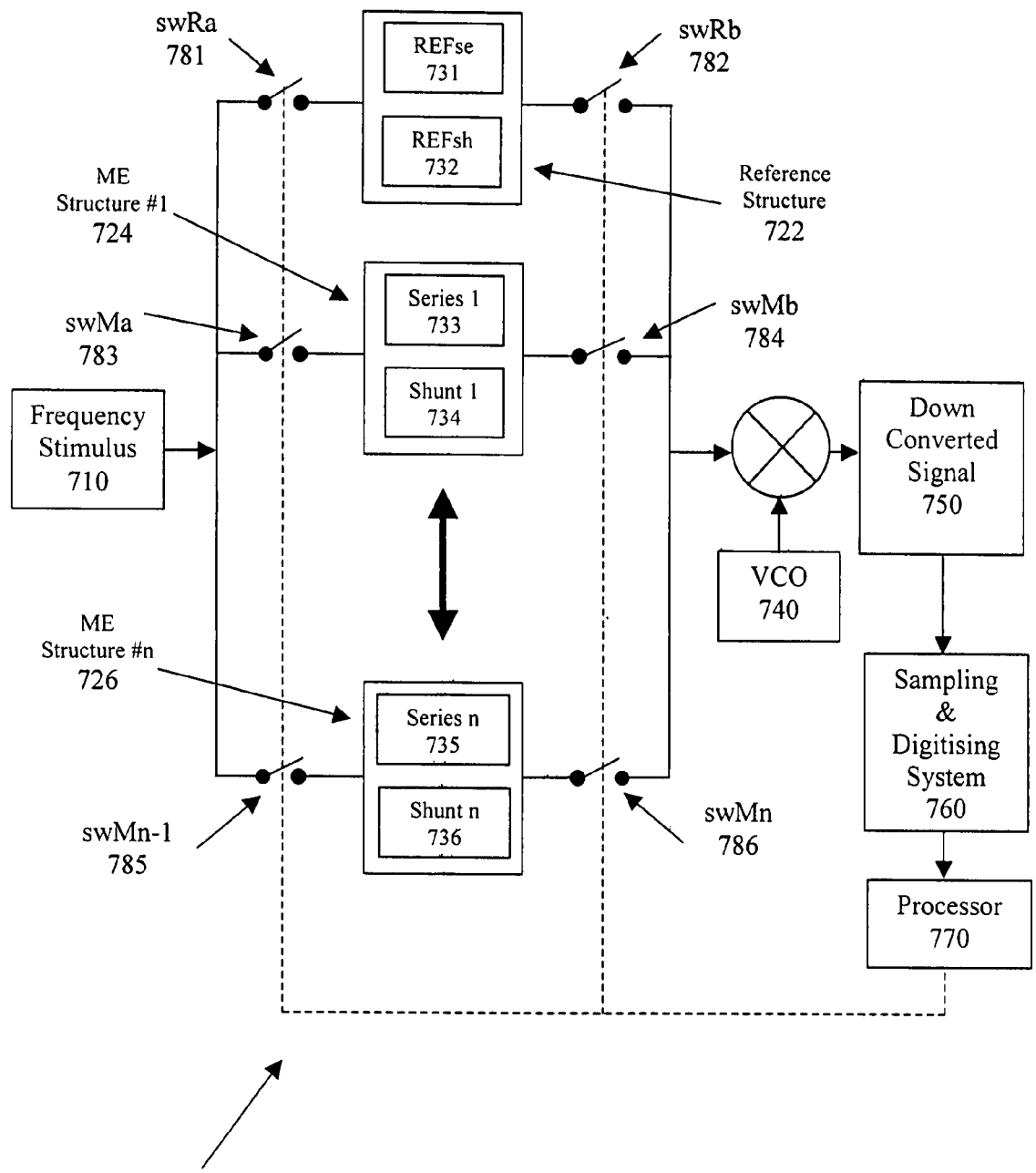
FIG. 7 is a similar view of a general multi-structure configuration.

The paired multi-element configuration 600 shown in FIG. 6 can be extended to include a general multi-structure configuration 700 such as shown in FIG. 7. A reference structure 722 comprises reference series multi-elements REFse 731 and reference shunt multi-elements REFsh 732. The reference structure 722 and its multi-elements REFse 731 and REFsh 732 would typically not have sensitive areas within them. The remaining multi-element (ME) structures, namely ME Structure #1 724 and up to and including ME Structure #n 726 would have sensitive areas such as MREs on each of their series and shunt elements. These sensitive areas would detect the same effects or different effects depending upon the sensor's application. ME Structure #1 724 comprises series multi-elements, namely Series 1 733 and its shunt multi-elements, namely Shunt 1 734. Similarly, ME Structure #n 726 would have series multi-elements, namely Series n 735 and shunt multi-elements, namely Shunt n 736. A matrix of switches, namely swRa 781, swRb 782, swMa 783, swMb 784 and continuing to swMn−1 785 and swMn 786 are controlled by the processor 770 to divert the frequency stimulus 710 to each of the multi-element structures, namely reference structure 722, ME Structure 1 724 continuing to ME Structure n 726. Also, to direct the outputs from the multi-element structures to the input of the mixer 730. The mixer 730 uses another frequency input from a VCO 740, to produce a modified down converted signal 750 at a lower frequency range than the resonant frequencies of the multi-element structures which are used to form a general multi-structure configuration 700. A selected down converted signal 750 is then suitably conditioned, sampled and digitised within the sampling and digitising system 760. The binary equivalent of the selected down converted signal 750 then acts as the input to a digital processor 770. This processor can then detect the magnitude and phase features of the frequency response characteristics of each of the multi-element structures, namely reference structure 722, ME Structure 1 724 continuing to ME Structure n 726, and produce data indicating a change due to the interaction of the sensitive areas within the detecting multi-element structures.

Figure 8:
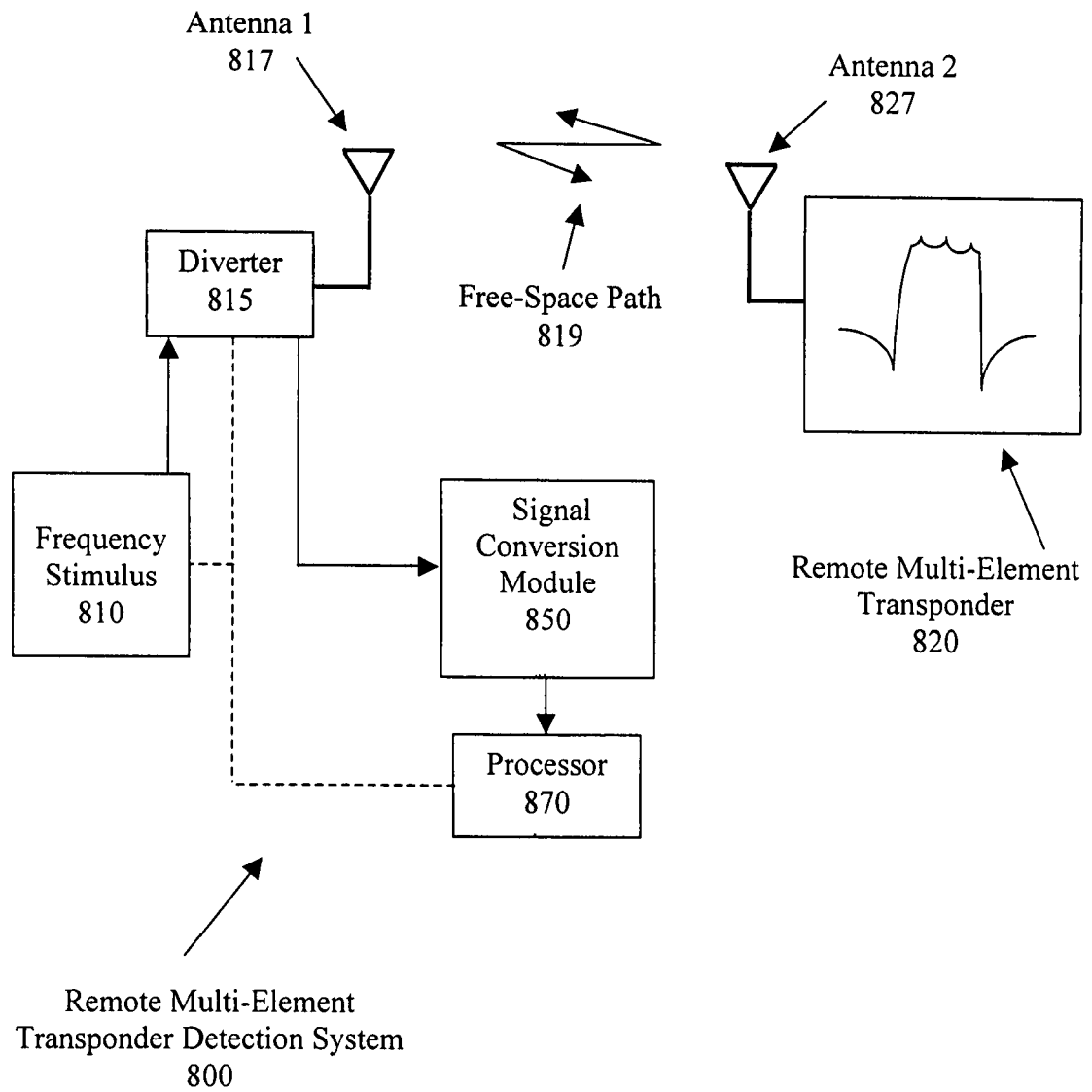
FIG. 8 is a similar view of a remote multi-element transponder detection system.

Remote interrogation of an acoustic wave sensor utilizing a multi-element structure in accordance with the invention can be obtained by modifying the multi-element detection system 500 shown in FIG. 5 to that of a remote multi-element transponder detection system 800 as shown in FIG. 8. The processor 870 controls the frequency stimulus 810 and a diverter 815. The diverter 815 changes the direction of the signal path so that, when a remote multi-element transponder 820 is interrogated, the diverter 815 enables the signal path to proceed from the frequency stimulus 810, through an antenna 1 817, via a free-space path 819 to an antenna 2 827 which is electrically connected to the remote multi-element transponder 820. The remote multi-element transponder 820 will return a signal which is dependent upon the perturbations occurring within the sensitive areas located within the remote multi-element transponder 820. The returned signal leaves the remote multi-element transponder 820 via antenna 2 827, propagates through the free-space path 819 to antenna 1 817 and is then directed through the diverter 815 by the processor 870 to a signal conversion module 850 and on to the processor 870 for further processing. This method of interrogating a remote multi-element transponder 820 permits more than two sensitive areas, such as MREs and more specifically antibodies, to be place on the remote multi-element transponder 820.

An acoustic wave sensor utilizing a multi-element structure in accordance with the invention may comprise SAWs, BAWs or FBARs, depending on the intended use of the sensor. For remote sensing, the use of BAW and FBAR devices for transponder applications is more challenging compared to the use of SAW RFID sensors such as described by P. J.

Figure 9:
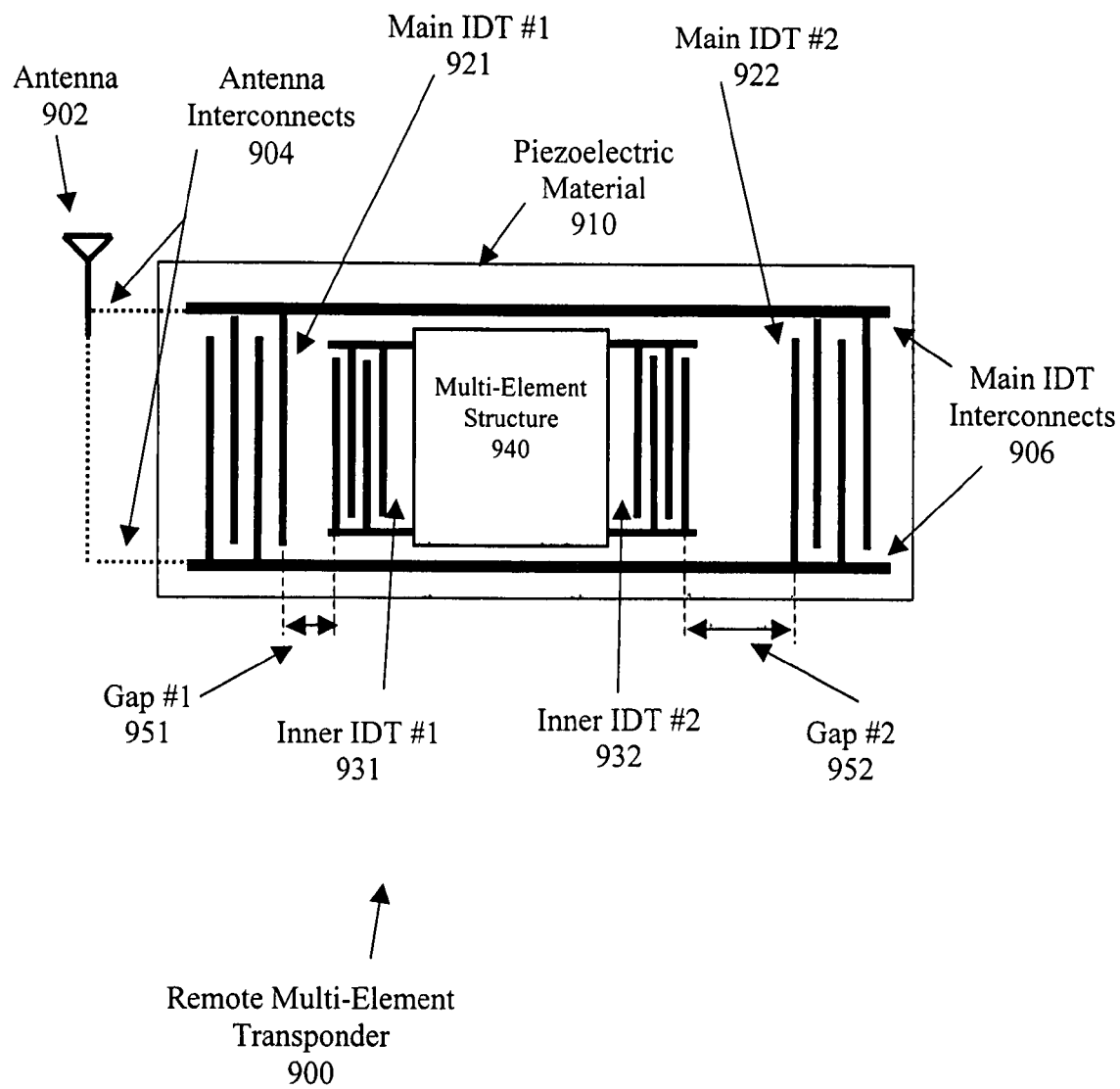
FIG. 9 is a similar view of a remote multi-element transponder.

Edmonson et al, A SURFACE ACOUSTIC WAVE SENSOR OR IDENTIFICATION DEVICE WITH BIOSENSING CAPABILITY, U.S. Pat. No. 7,053,524 B2 issued May 30, 2006. A remote multi-element transponder 900 as shown in FIG. 9 utilizes a nested SAW type structure, such that SAW type of propagation devices along with BAW and FBAR type devices can be assembled as multi-element configurations.

An antenna 902 receives an interrogation signal and, using antenna interconnects 904, the signal passes through main IDT interconnects 906 which are located on a suitable piezoelectric material 910. The main IDT #1 921 and the main IDT #2 922 are also located on the piezoelectric material 910 and are electrically connected to the main IDT interconnects 906. The interrogation signal on the main IDT interconnects 906 then excites both of the main IDTs 921, 922, and acoustic waves propagate bi-directionally from the main IDTs 921, 922. A second SAW device is located in the propagation path of the acoustic waves and comprises an inner IDT #1 931 and an inner IDT #2 932 located on the piezoelectric material 910 and electrically connect to a multi-element structure 940. The multi-element structure 940 may include BAW, FBAR and SAW type resonators, depending on the intended use of the sensors. The multi-element structure 940 is spaced from the piezoelectric material 910 but is electrically connected to the inner IDTs 931, 932.

An acoustic wave propagating from the main IDT #1 921 interacts with the inner IDT #1 931 to cause an electrical signal to interact with the multi-element structure 940. An electrical signal, modified by interaction with the multi-element structure 940, causes an acoustic wave to propagate from the inner IDT #2 932 and interact with the main IDT #2 922, causing a modified electrical signal to connect to the antenna 902 via the main IDT interconnects 906 and the antenna interconnects 904 and be returned back to the interrogator.

Even though a single interrogation signal is presented to the remote multi-element transponder 900, several modified returned signals result, due to the nature of the acoustic waves propagating bi-directionally from the main IDTs 921, 922 and from the inner IDTs 931, 932. Another feature of this embodiment is the asymmetry of the nested SAWs comprising inner IDTs 931, 932) and the multi-element structure 940. The acoustic wave propagation distance from the main IDT #1 921 to the inner IDT #1 931 is defined as Gap #1 951, and the acoustic wave propagation distance from the main IDT #2 922 to the inner IDT #2 932 is defined as Gap #2 952. Gap #1 951 differs from Gap #2 952 such that, during any one time event, there is only one set of electrical signals generated from either the inner IDT #1 931 or from the inner IDT #2 932 within the multi-element structure 940 at one time.

Another feature of the remote multi-element transponder 900 is the ability of utilizing harmonic features within the main IDTs 921, 922 and the inner IDTs 931, 932. Harmonic IDTs, such as described by C. K. Campbell and P. J. Edmonson, "An Empirical Method For Obtaining The Harmonic Response Coefficients Of A SAW Interdigital Transducer," 2002 IEEE Ultrasonics Symposium, Munich, Germany, October 2002, can operate at multiples of a center frequency $f_o$. This feature permits, for example, an FBAR multi-element structure 940, spaced from the piezoelectric material 910, to operate at 3,000 MHz center frequency, while the main IDTs 921, 922 and the inner IDTs 931, 932 located on the piezoelectric material 910, can be geometrically structured at a frequency equal to 3,000 MHz divided by "n", where "n" is the harmonic value. This feature permits simplification of the photolithographic process used to construct the main IDTs 921, 922 and the inner IDTs 931, 932.

One use for an acoustic wave sensor utilizing a multi-element structure in accordance with this invention is for the rapid detection of sepsis. Sepsis is a cascading failure of organ systems, usually initiated by infection of the blood, then exacerbated by a massive, injurious inflammatory response. Typically there are about 18 million cases of severe sepsis per year worldwide. The present invention enables two different types of biomarkers to be detected simultaneously in real time from a subject's breath. The first type of biomarker is representative of the earliest physiological responses to infection, where blood circulation is re-distributed at the expense of the gut. The gut responds by sending out several secreted signaling biomarkers in response to relative low oxygenation. The signaling biomarkers include but are not limited to, endothelin-1 (ET-1), erythropoietin (EPO) and tumour necrosis factor-alpha (TNF-α). The second type of biomarker is representative of bacteria which includes, but is not limited to, lipopolysaccharide (LPS), a bacterial wall component.

Figure 10:
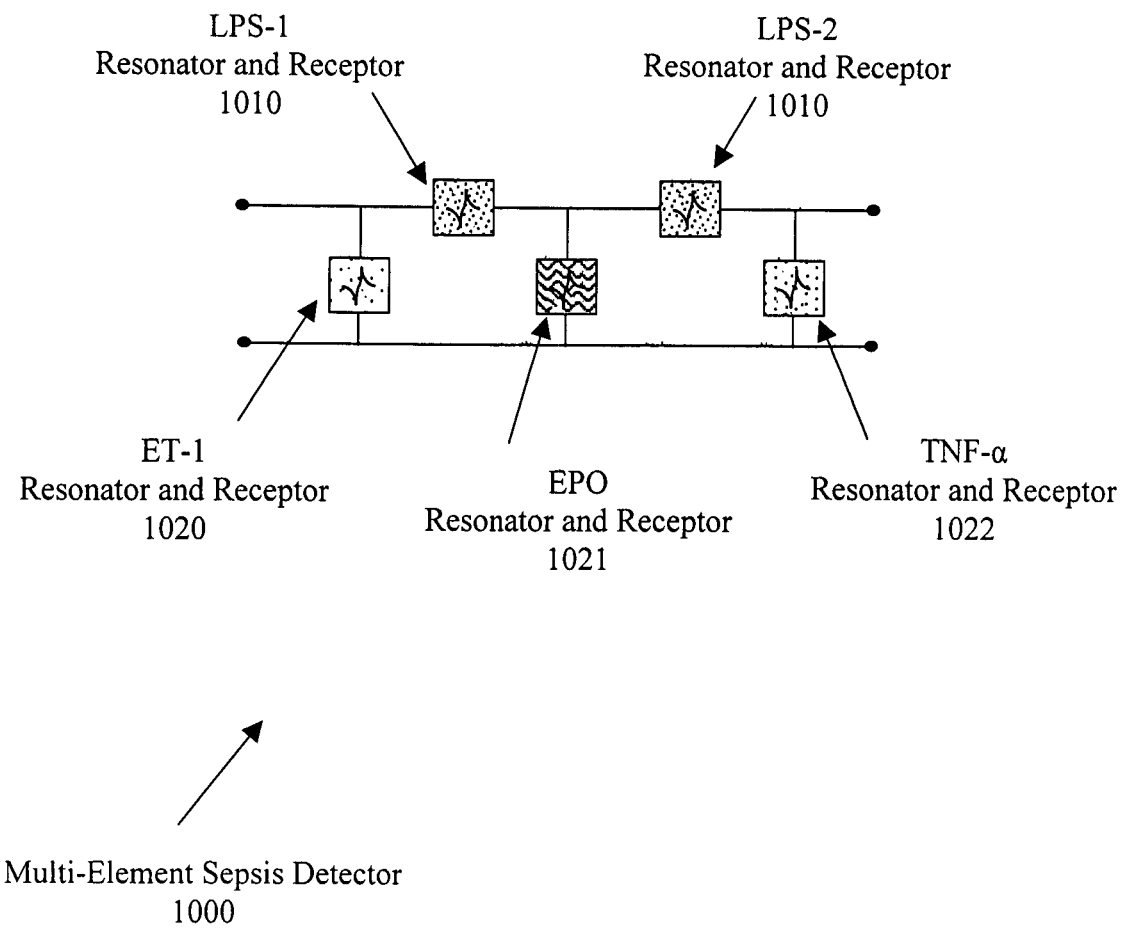
FIG. 10 is a similar view of a multi-element sepsis detector.

An example of how an acoustic wave sensor utilizing a multi-element structure in accordance with this invention can be used as a multi-element sepsis detector 1000 is shown in FIG. 10. Three separate and different shunt elements contain an ET-1 resonator and receptor 1020, an EPO resonator and receptor 1021 and a TNF-A resonator and receptor 1022. The series elements LPS-1 resonator and receptor 1010 and LPS-2 resonator and receptor 1011 are also separate but contain the same lipopolysaccaride receptor.

This duplication maintains the integrity of the ladder structure and also provides a method of redundancy. Sensitive bedside measures of biomarkers for the early detection of sepsis can give clinicians time to initiate therapies which prevent disease progression. Monitoring the contents of breath for diagnostic and treatment purposes is not new, but has mostly been considered for lung diseases, since breath is an ideal window into lung function. The recognized need for better sensors of breath contents prompted a consensus study by Horvath, et al., "Exhaled breath condensate: methodological recommendations and unresolved questions" *Eur Respir J*, vol. 26, no. 3, pp. 523-548, 2005, highlighting the potential for clinical use in myriad lung diseases, as well as current technical limitations. An acoustic wave sensor utilizing a multi-element structure in accordance with the present invention can be arranged to check the breath of a subject and provide a rapid diagnosis of sepsis. Similarly, an acoustic wave sensor utilizing a multi-element structure in accordance with the invention could be used for the detection of biological or chemical molecules in any biological fluid including, but not limited to, blood, saliva, and urine.

Other embodiments and advantages of the invention will now be readily apparent to a person skilled in the art from the foregoing description, a scope of the invention being defined in the appended claims.

The invention claimed is:

1. An acoustic wave sensor assembly including:
   piezoelectric material;
   a first acoustic wave resonator element structure mounted on the piezoelectric material for interacting with an electrical signal;
   said acoustic wave resonator element structure being operable to interact with an acoustic wave propagating within the piezoelectric material to produce a first frequency response;
   further acoustic wave resonator element structures mounted on the piezoelectric material for interacting with electrical signals;
   said further acoustic wave resonator element structures being operable to interact with further acoustic waves propagating within the piezoelectric material to produce subsequent frequency responses;

said first acoustic wave resonator element structure and further acoustic element structure and further acoustic wave resonator element structures being combined to form a ladder or lattice filter network to produce an overall frequency response; and sensitive areas mounted on the piezoelectric material and associated with the acoustic wave resonator element structures which, if predetermined effects to be sensed or detected are present, are modified thereby to control the nature of the frequency response and thereby provide information with respect to the predetermined effects to be sensed or detected.

2. A sensor assembly according to claim 1 wherein the piezoelectric material and acoustic wave resonator element structures form a ladder filter network.

3. A sensor assembly according to claim 1 wherein the piezoelectric material and acoustic wave resonator element structures form a lattice filter network.

4. A sensor assembly according to claim 1 wherein the acoustic wave resonator element structures are placed on the same body of piezoelectric material.

5. A sensor assembly according to claim 1 wherein the acoustic wave resonator element structures are placed on separate bodies of piezoelectric material.

6. A sensor assembly according to claim 1 wherein the acoustic wave resonator element structures have subsets devoid of sensitive areas, said subsets of acoustic wave element structures being combined with other acoustic wave resonator element structures.

7. A sensor assembly according to claim 1 wherein the acoustic wave resonator element structures can be interrogated by a frequency stimulus.

8. A sensor assembly according to claim 7 wherein interrogation is effected wirelessly.

9. A sensor assembly according to claim 8 wherein interrogation is effected by sets of interdigital transducers (IDTs), said interdigital transducers being located on remote piezoelectric material.

10. A sensor assembly according claim 9 wherein the acoustic wave resonator element structures are located within the sets of interdigital transducers.

11. A sensor assembly according to claim 10 wherein the acoustic wave resonator element structures are spaced from the piezoelectric material.

12. A sensor assembly according to claim 11 wherein the acoustic wave resonator element structures are electronically connected to the inner set of interdigital transducers.

13. A sensor assembly according to claim 1 where at least one sensitive area comprises molecular recognition elements (MREs).

14. A sensor assembly according to claim 1 where at least one sensitive area comprises antibodies.

15. A sensor assembly according to claim 1 where at least one sensitive area comprises endothelin-1 (ET-1) receptors.

16. A sensor assembly according to claim 1 where at least one sensitive area comprises erythropoietin (EPO) receptors.

17. A sensor assembly according to claim 1 where at least one sensitive area comprises tumour necrosis factor-alpha (TNF-α) receptors.

18. A sensor assembly according to claim 1 where at least one sensitive area comprises lipopolysaccharide (LPA) receptors.

* * * * *